United States Patent
Flanagan

(10) Patent No.: US 7,628,807 B2
(45) Date of Patent: Dec. 8, 2009

(54) STENT FOR DELIVERING A THERAPEUTIC AGENT HAVING INCREASED BODY TISSUE CONTACT SURFACE

(75) Inventor: Aiden Flanagan, Galway (IE)

(73) Assignee: Boston Scientific Scimed, Inc., Maple Grove, PA (US)

( * ) Notice: Subject to any disclaimer, the term of this patent is extended or adjusted under 35 U.S.C. 154(b) by 307 days.

(21) Appl. No.: 10/982,356

(22) Filed: Nov. 4, 2004

(65) Prior Publication Data

US 2006/0095123 A1 May 4, 2006

(51) Int. Cl.
*A61F 2/06* (2006.01)
(52) U.S. Cl. .................................... 623/1.42
(58) Field of Classification Search ........ 623/1.15–1.48
See application file for complete search history.

(56) References Cited

U.S. PATENT DOCUMENTS

| | | | |
|---|---|---|---|
| 4,733,665 A | 3/1988 | Palmaz | |
| 4,994,071 A | 2/1991 | MacGregor | |
| 5,397,355 A | 3/1995 | Marin et al. | |
| 5,421,955 A | 6/1995 | Lau et al. | |
| 5,527,354 A | 6/1996 | Fontaine et al. | |
| 5,562,728 A | 10/1996 | Lazarus et al. | |
| 5,628,787 A | 5/1997 | Mayer | |
| 5,707,387 A | 1/1998 | Wijay | |
| 5,718,713 A | 2/1998 | Frantzen | |
| 5,733,326 A | 3/1998 | Tomonto et al. | |
| 5,815,904 A | 10/1998 | Clubb et al. | |
| 5,902,475 A | 5/1999 | Trozera et al. | |
| 5,976,182 A * | 11/1999 | Cox ......................... | 623/1.1 |
| 6,475,233 B2 | 11/2002 | Trozera | |
| 6,478,816 B1 | 11/2002 | Kveen et al. | |
| 6,652,575 B2 * | 11/2003 | Wang ....................... | 623/1.15 |
| 6,758,859 B1 | 7/2004 | Dang et al. | |
| 7,156,869 B1 * | 1/2007 | Pacetti ..................... | 623/1.11 |
| 2001/0010014 A1 | 7/2001 | Trozera | |
| 2002/0038767 A1 | 4/2002 | Trozera | |
| 2002/0091438 A1 | 7/2002 | Trozera | |
| 2002/0138133 A1 | 9/2002 | Lenz et al. | |
| 2003/0065382 A1 * | 4/2003 | Fischell et al. ............ | 623/1.15 |
| 2003/0088307 A1 * | 5/2003 | Shulze et al. .............. | 623/1.15 |

FOREIGN PATENT DOCUMENTS

| | | |
|---|---|---|
| EP | 1300166 A | 4/2003 |
| WO | WO 98/53760 A | 12/1998 |
| WO | WO 2005/115276 A | 12/2005 |

* cited by examiner

*Primary Examiner*—Suzette J Gherbi
(74) *Attorney, Agent, or Firm*—Vidas, Arrett & Steinkraus

(57) ABSTRACT

A stent for implantation in a body lumen is described comprising at least one strut having an inner surface, an outer surface, a first side surface disposed between the inner surface and the outer surface, and a second side surface disposed between the inner surface and the outer surface; wherein the first side surface and the second side surface converge toward one another in the direction of the outer surface; and a coating comprising a therapeutic agent disposed on at least a portion of a surface of the strut.

18 Claims, 7 Drawing Sheets

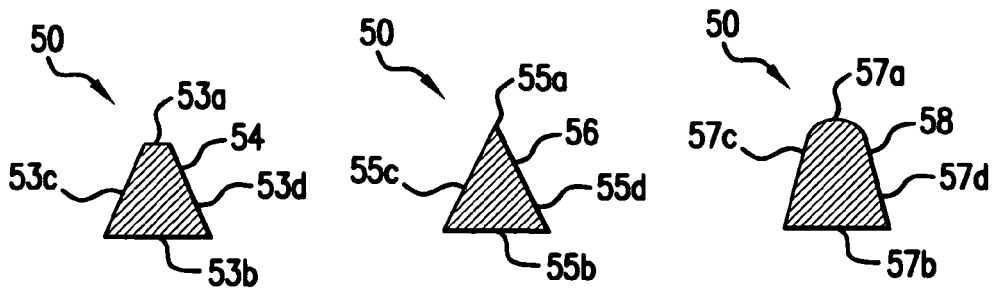
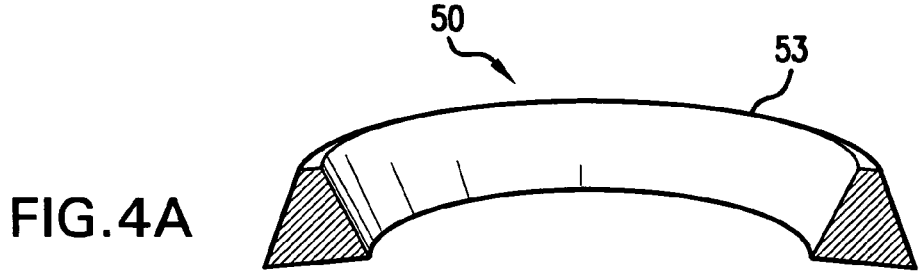
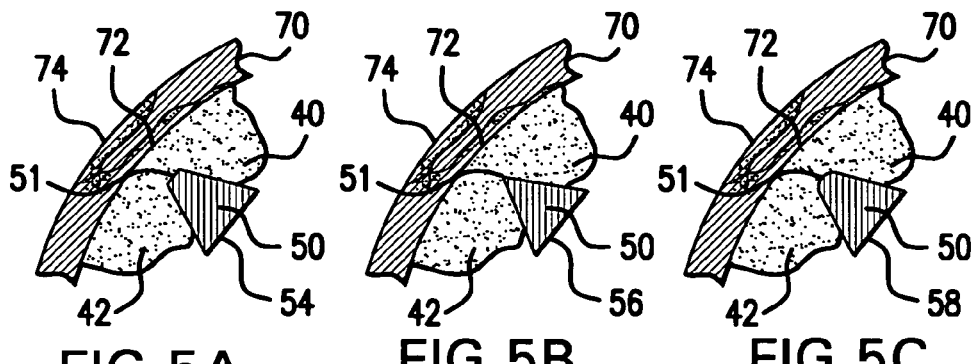

STENT FOR DELIVERING A THERAPEUTIC AGENT HAVING INCREASED BODY TISSUE CONTACT SURFACE

FIELD OF THE INVENTION

This invention relates generally to medical devices, such as stents, for delivering a therapeutic agent to body tissue of a patient, such as a body lumen. More particularly, the invention is directed to a stent comprising at least one strut having increased body tissue contact surface. The invention is also directed to a method for delivering therapeutic agents to body tissue of a patient.

BACKGROUND OF THE INVENTION

A variety of medical conditions have been treated by introducing an insertable medical device having a coating for release of a therapeutic agent. For example, various types of medical devices coated with a therapeutic agent, such as stents, have been proposed for localized delivery of such agents to a body lumen. See, e.g., U.S. Pat. No. 6,099,562 to Ding et al issued on Aug. 8, 2000. However, it has been noted that, existing coated medical devices can be improved. For instance, the release profile of a therapeutic agent from the coated medical device may not be accurate or precise in relation to a target tissue site.

In the case of stents, drug-eluting stents are typically stents with a polymeric coating which includes a therapeutic agent. The polymer generally contains a therapeutic agent to, for example, prevent restenosis in a vessel after implantation of a stent. The drug may then be released from a stent into a tissue surface in a controlled manner. Generally, the therapeutic agent is typically only released from the area closest to the outer surface of the coating, leaving a significant amount of therapeutic agent in the coating. Also, current struts generally have rectangular or square outer surfaces. These designs may lead to drug-release at undesirably limited locations thereby not adequately delivering the drug to a target tissue site or vessel wall. This is at least in part due to the fact that at least one surface of a rectangular or square strut is facing away from a tissue surface after a stent has been implanted.

More particularly, FIG. 1 shows a stent strut 5 of a stent that is implanted into a blood vessel 1 having an obstruction 3, such as plaque resulting from restenosis. The strut 5 may have a rectangular shaped cross-section and four sides: an outer surface 5a, which contacts the obstruction 3; an inner surface 5b, which is opposite the outer surface 5a, and two side surfaces or side walls 5c and 5d which connect the outer and inner surfaces 5a and 5b. A coating 7 may be disposed on the four surfaces 5a, 5b, 5c and 5d. As shown in FIG. 1, generally, when the stent with struts having rectangular-shaped cross-sections is implanted, only the outer surface 5a is in intimate contact with the obstruction 3 or blood vessel wall. Therefore, release of the drug or therapeutic agent from the coating is primarily from the outer surface 5a of the stent. Some therapeutic agent can be released from the inner surface 5b and side surfaces 5c and 5d to the obstruction 3 or vessel wall. However, generally the therapeutic agent releases into the blood before reaching the obstruction 3 or blood vessel wall. Thus, it is expected that only a small amount of the therapeutic agent that is released from the inner surface 5b and side surfaces 5c and 5d reaches the obstruction or blood vessel. Also, because therapeutic agents, such as paclitaxel, are lipophillic, the coating generally should be in close contact with the cell walls of the cells that are to be treated for efficient release of the lipophillic agent since cell walls are composed of fat. Since the inner surface 5b and side surfaces 5c and 5d of the coated strut generally do not contact cells to be treated but instead contacts blood, the release of lipophillic drugs from these surfaces tends to be slow.

Inefficient drug release patterns, such as described above, may result in the use of an undesirably high amount of therapeutic agents in a medical device coating to achieve a desired amount of treatment on a target tissue site. Another undesirable result may be the release of unwarranted therapeutic agents directly into the bloodstream. For these and other reasons, there is a need for medical devices, such as stents, with outer surface configurations that more accurately and precisely deliver therapeutic agents to target sites without concurrently releasing undesirably high amounts of such agents away from a target tissue site.

Furthermore, it may be preferable to have a stent with struts that have greater contact with the tissues or cells to be treated. More specifically, it would be desirable to have struts that have coated side surfaces that directly contact the tissue to further more effective release of therapeutic agents from the coated side surfaces to the tissue to be treated. Thus, there exists a need for such a device to more efficiently deliver therapeutic agents to tissue sites.

SUMMARY OF THE INVENTION

The present invention addresses these objectives by providing a stent having struts with increased contact area with the tissue into which the stent is implanted. Such increased contact area promotes release of therapeutic agent from a coating disposed on the surfaces of the struts. More specifically, the struts have cross-sections that taper towards the outer surface of the strut, i.e., the surface that faces away from the flow path of the stent. This tapered configuration allows the strut to penetrate into the tissue into which the stent is implanted e.g., obstruction or blood vessel wall, thereby increasing the contact area between the strut surfaces and the tissue. This increased contact area in turn promotes release of the therapeutic agent from the coating disposed on the strut surfaces into the tissue, which can reduce the dose of therapeutic agent used. Also, the increased contact area with the tissue reduces the amount of therapeutic agent releases into the blood stream.

In one embodiment, a stent for implantation in a body lumen is described, comprising at least one strut having an inner surface, an outer surface, a first side surface disposed between the inner surface and the outer surface, and a second side surface disposed between the inner surface and the outer surface and in contact with the outer surface; wherein the first side surface and the second side surface converge toward one another in the direction of the outer surface; and a coating comprising a therapeutic agent disposed on at least a portion of a surface of the strut. The stent may be a intravascular stent.

The coating may be disposed on at least a portion, or any combination, of the outer surface, the first side surface, and/or the second side surface. The coating may be a therapeutic agent, and may comprise an antibiotic, paclitaxel or a derivative thereof, rapamycin, tacrolimus, or everolimus, or a combination thereof. The coating may also be a polymeric material, and the polymeric material may incorporate a therapeutic agent.

The strut may have a cross-section having a substantially triangular, trapezoidal, or curved shape, or any combination thereof.

The stent may further comprise a third side surface disposed between the inner surface and the outer surface and in contact with the inner surface, and a fourth side surface disposed between the inner surface and the outer surface and in contact with the inner surface.

In another embodiment, a stent for implantation in a body lumen is described, comprising at least one strut having an inner surface, an outer surface, a first side surface disposed between the inner surface and the outer surface, and a second side surface disposed between the inner surface and the outer surface; wherein the first side surface and the second side surface converge toward one another in the direction of the outer surface; and a coating comprising a therapeutic agent and a polymeric material disposed on at least a portion of the outer surface, a portion of the first side surface, and a portion of the second side surface.

In yet another embodiment, an intravascular stent for implantation in a body lumen is described, comprising at least one strut having an inner surface, an outer surface, a first side surface disposed between the inner surface and the outer surface and in contact with the outer surface, and a second side surface disposed between the inner surface and the outer surface and in contact with the outer surface; wherein the first side surface and the second side surface converge toward one another in the direction of the outer surface; and wherein the strut comprises a cross-section having a substantially trapezoidal shape in which the first side surface and the second side surface form the sides of the substantially trapezoidal shape; and a coating comprising a polymeric material incorporating a therapeutic agent disposed on at least a portion of the outer surface, a portion of the first side surface, and a portion of the second side surface.

The present invention further aims to combine the advantages of stents with increased surface area, while still maintaining the advantages of flexible stent designs. Stents with increased surface area are advantageous because they present more coating options for drug delivery. Flexible stents are advantageous because they allow for the stent to better travel through the anatomy of a patient to a targeted tissue within the body. However, certain previous designs of stents with increased surface area suffer from low flexibility because the increase in surface area is generally accomplished by adding more struts to the stent and/or increasing the thickness of the struts, thereby increasing the mass of the stent. Certain previous designs of stents with increased flexibility suffer from low carrying capacity for drug delivery, as higher flexibility was generally accomplished by providing less struts over the length of the stent. The present invention combines both advantages by avoiding these drawbacks by providing various strut surface shapes and drug coating patterns to create a flexible stent with increased surface area.

BRIEF DESCRIPTION OF THE DRAWINGS

FIGS. 3A-3C are partial cross-sectional views of a strut taken along the line A-A of the stent of FIG. 2B, showing strut cross-section having trapezoidal, triangular, and curved trapezoidal configurations, respectively;

FIGS. 4A-4C are enlarged partial views of a strut of the stent of FIG. 2B, showing trapezoidal, triangular, and curved trapezoidal cross-section configurations, respectively;

FIGS. 5A-5C are side views of the configurations of FIGS. 3A-3C, respectively, implanted into and penetrating a tissue surface;

DETAILED DESCRIPTION OF THE INVENTION

Figure 2A:
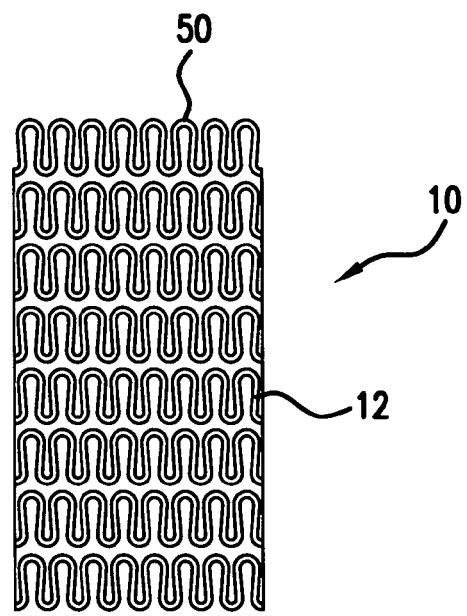
FIG. 2A is a top view of an exemplary stent with radially expandable cylindrical elements.
Figure 2B:
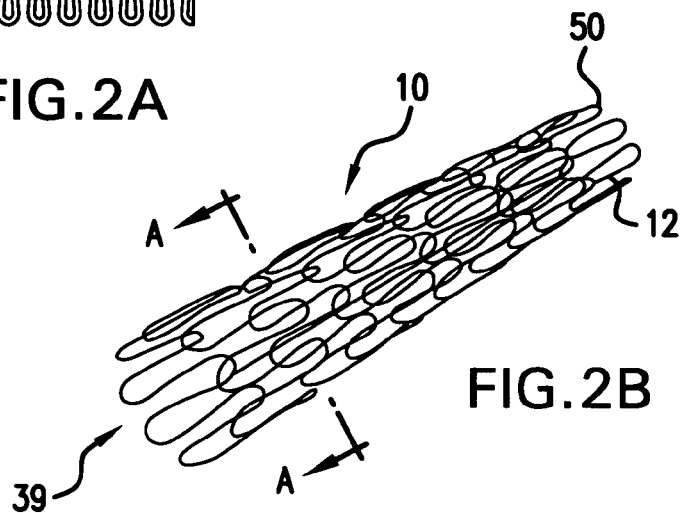
FIG. 2B is an oblique view of the stent of FIG. 2A in an unexpanded state.
Figure 2C:
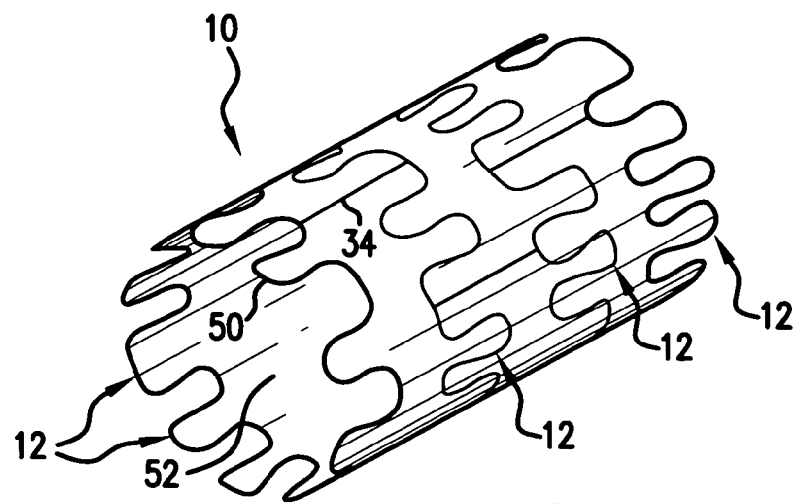
FIG. 2C is an oblique view of an exemplary stent of FIG. 2B with radially expandable cylindrical elements connected by connecting elements in an expanded state.

FIGS. 2A-2C show exemplary embodiments of a stent 10 that is suitable for use in the present invention. The stent 10 may have a flow path 52 therethrough. Stent 10 may also comprise a plurality of radially expandable cylindrical elements, and further may generally comprise struts 50 having a "peak" and "trough" configuration to form alternating loops. Adjacent radially expandable cylindrical elements 12 may be formed if at least two struts 50 are be connected to at least one connecting element 34. The connecting elements may be configured and situated to increase stability and/or flexibility of the stent. A more detailed discussion of stent configuration can be seen, inter alia, in U.S. Pat. No. 6,478,816 to Kveen et al., for "Stent", issued on Nov. 12, 2002, incorporated herein by reference in its entirety. Although the struts in this stent are shown to have a sinusoidal configuration, the struts can be straight. Generally, struts are wire-like elements or bar-like elements that make up a stent.

Other suitable stents include, for example, intravascular stents such as self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 5,449,373 issued to Pinchasik et al.

Stents that are suitable for the present invention may be fabricated from metallic, ceramic, or polymeric materials, or a combination thereof. Metallic materials are more preferable. Suitable metallic materials include metals and alloys based on titanium (such as nitinol, nickel titanium alloys, thermo-memory alloy materials), stainless steel, tantalum, nickel-chrome, or certain cobalt alloys including cobalt-chromium-nickel alloys such as Elgiloy® and Phynox®. Metallic materials also include clad composite filaments, such as those disclosed in WO 94/16646.

Suitable ceramic materials include, but are not limited to, oxides, carbides, or nitrides of the transition elements such as titaniumoxides, hafnium oxides, iridiumoxides, chromium oxides, aluminum oxides, and zirconiumoxides. Silicon based materials, such as silica, may also be used.

The polymer(s) useful for forming the stent should be ones that are biocompatible and avoid irritation to body tissue. They can be either biostable or bioabsorbable. Suitable polymeric materials include without limitation polyurethane and its copolymers, silicone and its copolymers, ethylene vinylacetate, polyethylene terephtalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

Other polymers that are useful as materials for stents include without limitation dacron polyester, poly(ethylene terephthalate), polycarbonate, polymethylmethacrylate, polypropylene, polyalkylene oxalates, polyvinylchloride, polyurethanes, polysiloxanes, nylons, poly(dimethyl siloxane), polycyanoacrylates, polyphosphazenes, poly(amino acids), ethylene glycol I dimethacrylate, poly(methyl methacrylate), poly(2-hydroxyethyl methacrylate), polytetrafluoroethylene poly(HEMA), polyhydroxyalkanoates, polytetrafluoroethylene, polycarbonate, poly(glycolide-lactide) co-polymer, polylactic acid, poly(y-caprolactone), poly(y-hydroxybutyrate), polydioxanone, poly(γ-ethyl glutamate), polyiminocarbonates, poly(ortho ester), polyanhydrides, alginate, dextran, chitin, cotton, polyglycolic acid, polyurethane, or derivatized versions thereof, i.e., polymers which have been modified to include, for example, attachment sites or cross-linking groups, e.g., RGD, in which the polymers retain their structural integrity while allowing for attachment of cells and molecules, such as proteins, nucleic acids, and the like.

Suitable stents may also be coated or made with non-polymeric materials. Examples of useful non-polymeric materials include sterols such as cholesterol, stigmasterol, β-sitosterol, and estradiol; cholesteryl esters such as cholesteryl stearate; $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; sphingomyelins such as stearyl, palmitoyl, and tricosanyl sphingomyelins; ceramides such as stearyl and palmitoyl ceramides; glycosphingolipids; lanolin and lanolin alcohols; and combinations and mixtures thereof. Preferred non-polymeric materials include cholesterol, glyceryl monostearate, glycerol tristearate, stearic acid, stearic anhydride, glyceryl monooleate, glyceryl monolinoleate, and acetylated monoglycerides.

FIGS. 3A-3C show partial cross-sectional views of struts 50 taken at line A-A of FIG. 2B. The struts base tapered contours which taper toward the outer surface 53a, 55a and 57a of the strut 50. FIG. 3A shows a cross-section with a substantially trapezoidal configuration or shape 54. The strut 50 has an outer surface 53a, which faces away from the flow path 52 of the stent, and an inner surface 53b, which faces the flow path 52. The strut 50 also has two side surfaces or 53c and 53d both of which are disposed between the inner surface 53b and outer surface 53b. Also, both the first and second side surfaces 53c and 53d are in contact with the outer surface 53a. Further, both side surfaces 53c and 53d converge toward each other in the direction of the outer surface 53a to form a tapered strut that tapers toward the outer surface. The side surfaces form the sides of the substantially trapezoidal shape.

FIG. 3B shows a strut cross-section having a substantially triangular shape or configuration 56. The strut 50 has an inner surface 55b which faces the flow path of the stent. The outer surface 55a in this configuration is the apex formed by the two converging side surfaces 55c and 55d which converge away from the inner surface 55b or toward the outer surface 55a. The side surfaces form the sides of the substantially triangular shape. The side surfaces 55c and 55d are disposed between the inner and outer surfaces 55b and 55a and are in contact with the outer surface 55a.

Like the struts shown in FIGS. 3A and 3B, the strut 50 in FIG. 3C has an outer surface 57a, which faces away from the stent flow path. However, in this embodiment, the outer surface 57a is substantially curved to form a curved trapezoid cross-section 58. As in the other embodiments the strut 50 has an inner surface 57b, which faces the stent flow path, and two side surfaces. The two side surfaces are disposed between the outer and inner surfaces 57a and 57b. Also, the side surfaces 57c and 57d converge toward the outer surface 57a and are in contact with the outer surface, 57a. It should be noted that while the inner surfaces and side surfaces of FIGS. 3A-3C are shown as being flat, they can also be curved like the outer surface 57a of FIG. 3C. Each strut configuration shown in FIG. 3A-3C allow the strut to increase the contact area between the strut surfaces and tissue as compared to struts having square or rectangular cross-sections.

Further, struts having different cross-sectional configurations may be used on a single stent. Moreover, a single strut element may have varying cross-sectional configurations over its length. For example, it may be preferable to design a stent 10 with a triangular cross-sectional configuration 56 along a length of the stent to align with a selected tissue area, but have a curved trapezoidal cross-sectional configuration 58 for the remainder of the length of the stent 10 for release on areas other than the selected tissue area.

FIGS. 4A-4C show enlarged partial side views of struts 50 that may be used with the stents of the invention. The cross-sectional configurations chosen for each strut in these embodiments remain constant throughout the length of the of the strut 50. As described above, it may be preferable for a strut 50 to have more than one configuration along the length of the strut 50.

FIGS. 5A-5C show the strut configurations of FIGS. 3A-3C, respectively, engaging a surface 40 of an obstruction 42 in a body lumen. The strut 50 may engage a tissue surface after stent 10 expands within a lumen. As shown, at least a portion of strut may engage and penetrate surface 40 of obstruction 42. The portion of strut 50 that penetrates the obstruction 42 may vary based at least in part on the expansion of stent 10, the cross-sectional configuration chosen for the strut 50, and the properties of the tissue surface. Alternatively, upon expansion of stent 10, the outer surface 51 of the strut 50 may rest adjacent to the surface 40 of an obstruction 42, wherein the outer surface 51 may apply pressure to surface 40 without actually penetrating the obstruction 42.

In the embodiments shown in FIGS. 5A-5C, outer surface 51 of strut 50 does not touch or penetrate inner wall 72 of vessel 70. It may be desirable to expand stent 10 to the extent that at least one outer surface 51 of strut 50 is brought into contact or penetrates inner wall 72. However, it may not be preferable for an outer surface 51 to penetrate an outer wall 74 of vessel 70.

A primary benefit of the embodiments of FIGS. 5A-5C is that a therapeutic agent coated on the stent may be released directly into an obstruction 42. This is particularly true when the strut penetrates into the obstruction or tissue to be treated. This may not only be preferable in concentrating agent release within obstruction 42 itself, but may also reduce agent dispersion in undesirable locations, such as directly into the bloodstream. Another benefit of these embodiments is that the embedding of at least a portion of the strut elements reduces the amount of vessel intima growth that needs to occur to effectively surround the stent struts. It is preferable that there is an amount of growth or "intimal hyperplasia" that occurs after the stent expands to at least partially envelop the struts into the body of the vessel wall, thereby removing a portion, and preferably all, of the stent from direct contact with the blood. The embodiments of FIGS. 5A-5C may allow for greater stent coverage by such growth, and reduce the time it takes to entirely envelop the stent within the vessel wall. However, it is possible to slow the growth of intimal hyperplasia while still retaining the structural advantages of the stent elements 50 of FIGS. 5A-5C by such methods and increasing the dose of therapeutic agent coated to the strut elements 50 (discussed below) or utilizing different pharmacokinetics.

Figure 6A:
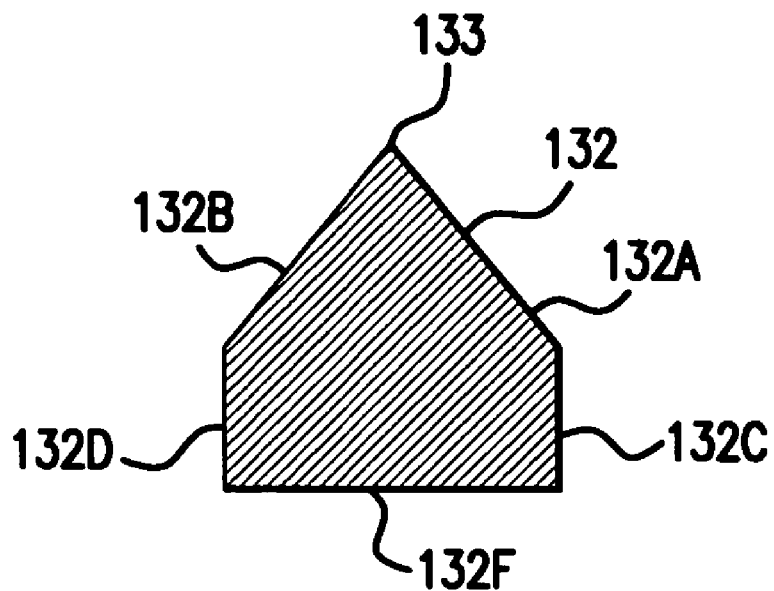
FIGS. 6A-6B show a strut cross-section having a partial triangular and partial trapezoidal configurations, respectively.
Figure 6B:
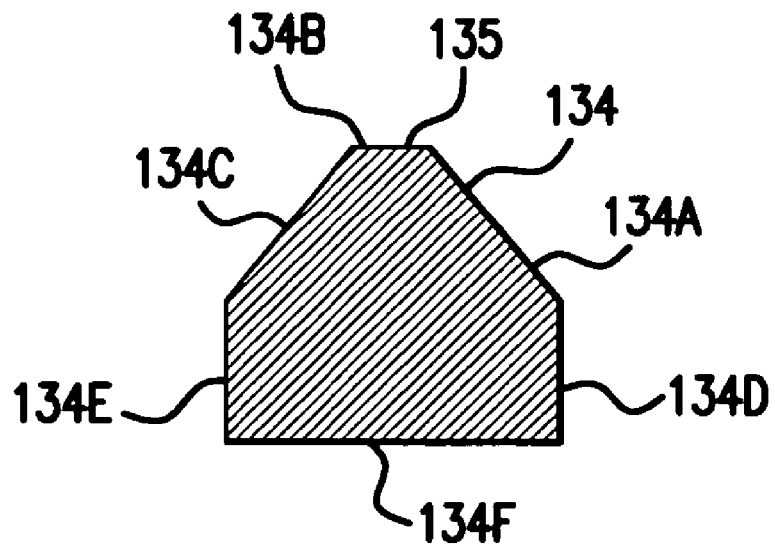
Figure 7A:
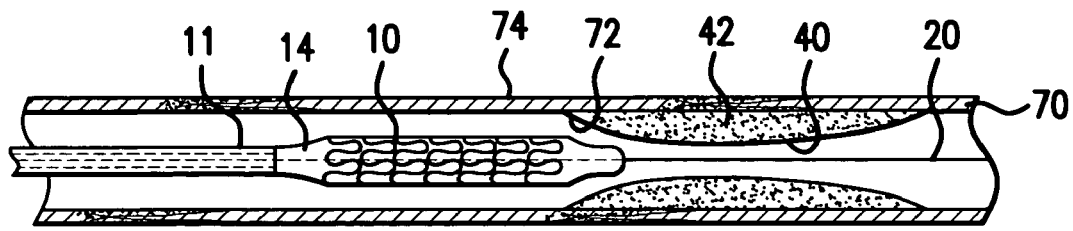
FIG. 7A is a top view, partially in section, of the stent of FIG. 2C in an unexpanded state within a body lumen, adjacent to a target tissue site.
Figure 7B:
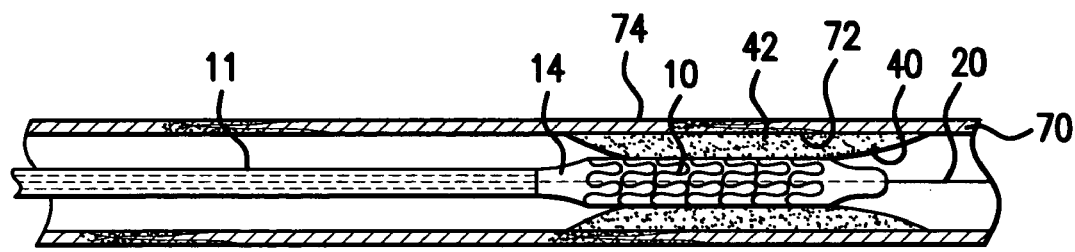
FIG. 7B is a top view, partially in section, of the configuration of FIG. 7A, wherein the unexpanded stent is positioned at the target tissue site.
Figure 7C:
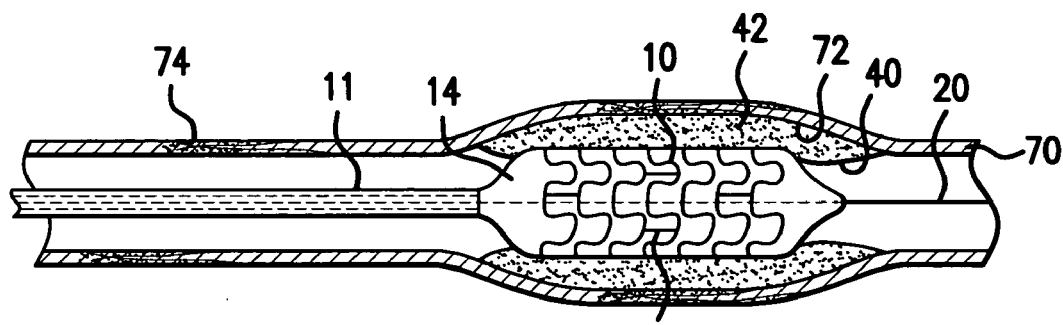
FIG. 7C is a top view, partially in section, of the configuration of FIG. 7B, wherein the stent is expanded and the struts are in contact with the target tissue site.
Figure 7D:
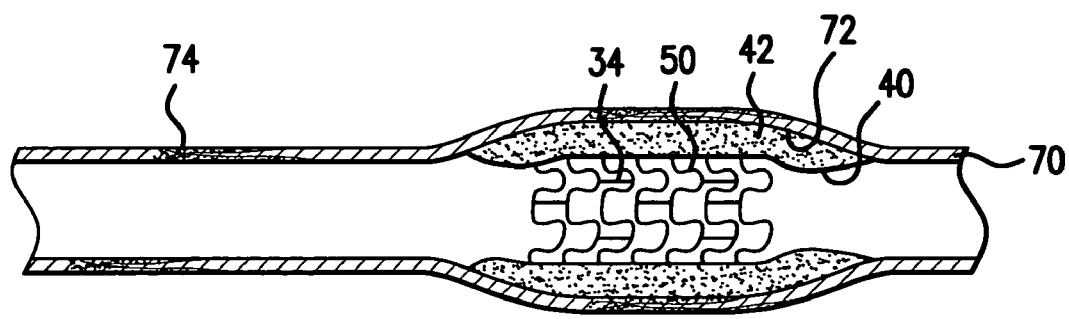
FIG. 7D is a top view, partially in section, of the configuration of FIG. 7C, wherein the delivery catheter is withdrawn and the stent is fully expanded.

FIGS. 6A-6B show further partial cross-sectional views of a strut 132 or 134 with a tapered cross-section that tapers toward the outer surface of the strut. FIG. 6A shows a strut, having a partial triangular cross-sectional configuration with outer surface 133. FIG. 6B shows a strut 134 having a partial trapezoidal cross-sectional configuration with outer surface 135. As compared to the configurations of FIGS. 3A-3C, the embodiments of FIGS. 6A-6B are less tapered and more closely resemble a rectangular cross-sectional configuration (not shown) of a conventional strut 50. However, the configurations of FIGS. 6A-6B may be preferable when it is desirable to maintain a higher volume of a strut element 50, for at least the purpose of increased stability. Furthermore, the strut 132 and 134 of FIGS. 6A-6B may be selectively coated with a biologically active agent in only the tapered side surfaces 132A-132B, and 134A-134C, as well as outer surfaces 133 and 135 thereby eliminating the release of a therapeutic agent from surfaces 132C, 132D, 134E and 134D. It should be noted that unlike the configuration of FIGS. 3A-3C, in the strut configurations of FIGS. 6A-6B, the converging side surfaces of the strut are in contact with the outer surface but not the inner surface. In these configurations, there is a third side surface 132D and 134D and a fourth side surface 132E and 134E, both of which are in contact with the inner surface 132F and 134E. In contrast, in FIGS. 3A-3C the converging side surfaces are in contact with both the inner and outer surfaces. Also, while not shown in the figures, there can be more than one surface between a converging side surface and the inner surface.

FIGS. 7A-7D show an exemplary delivery of a stent 10 into a body lumen. Stent 10 may first be mounted onto an inflatable balloon 14, or other mechanical delivery system, on the distal end of a delivery catheter 11. Stent 10 may be crimped or collapsed in substantially congruent dimensions to balloon 14. Guidewire 20 may be coaxially disposed in the body lumen prior to the introduction of the stent 10. Stent 10 and catheter 11 may then be introduced into a patient's body by methods such as the Seldinger technique, or other useful methods. Stent 10 and catheter 20 may be advanced over guidewire 20, at least to the area of obstruction 42. It may be preferable to advance the stent 10 until it is substantially centered in the area of obstruction 42.

When stent 10 is inserted into a desired location within a patient, balloon 14 may be inflated, which may thereby expand stent 10. At least one strut element 50 of stent 10 may thereby be brought into contact with at least a portion of the surface 40 of the obstruction 42 and/or the inner wall 72 of a vessel 70. Vessel 70 may be expanded slightly by the expansion of stent 10 to provide volume for the expanded lumen. As a result, interference of blood flow by stent 10 may be minimized, in addition to preventing unwarranted movement of stent 10 once the expansion is complete.

Figure 1:
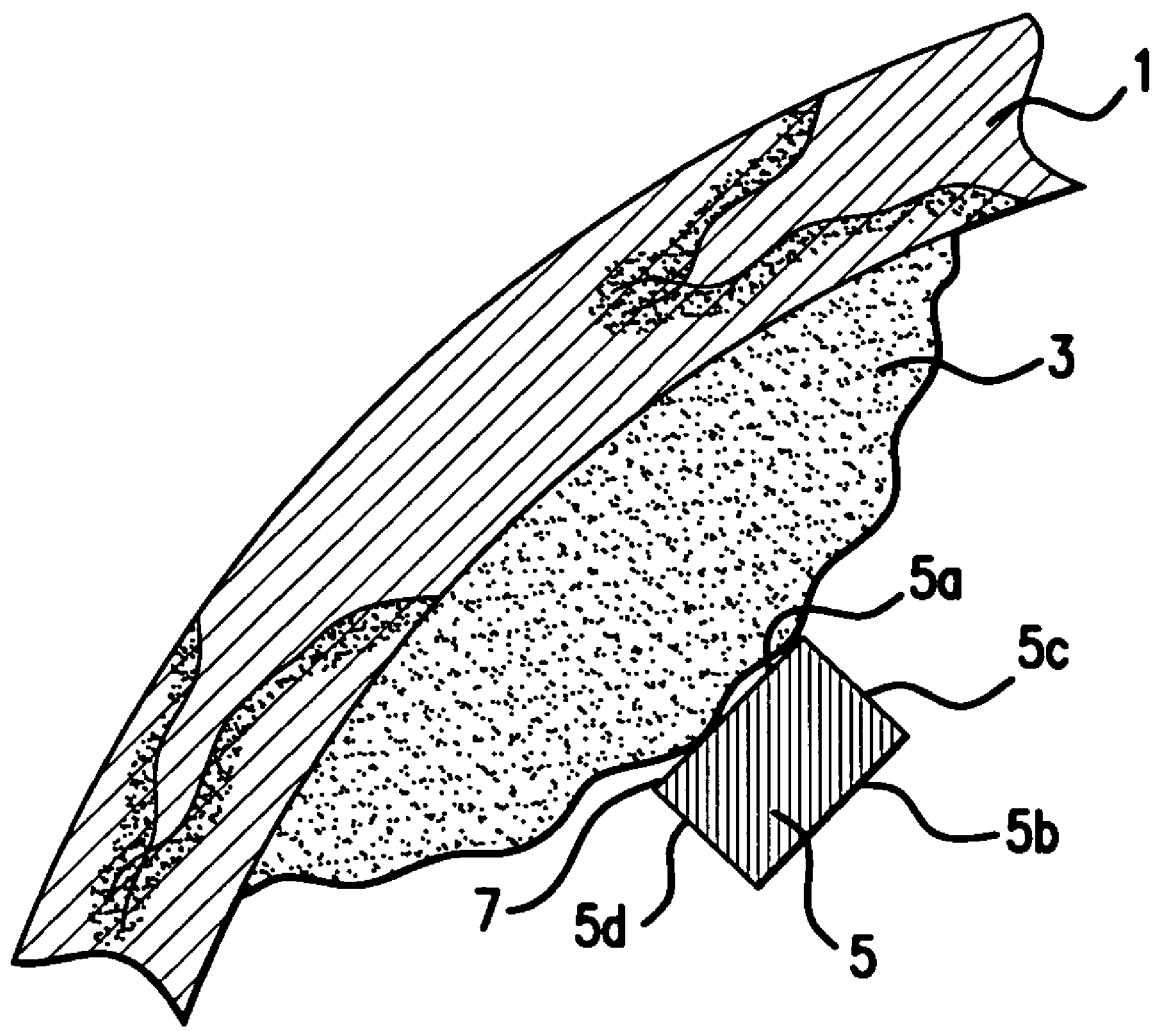
FIG. 1 is a cross-sectional view of a stent strut having a rectangular shape cross-section implanted in a blood vessel.
Figure 8A:
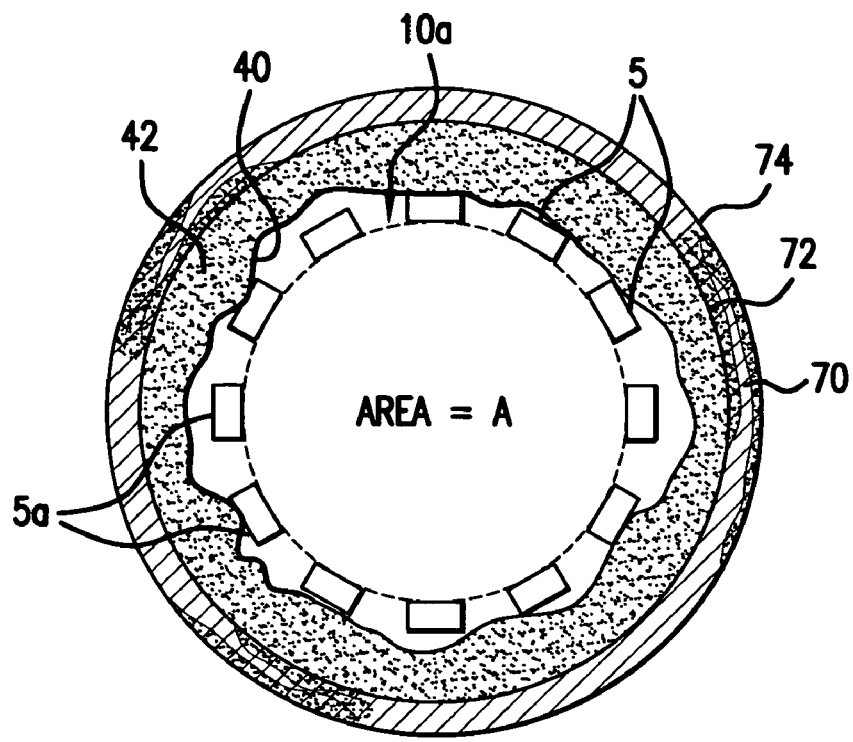
FIG. 8A shows a cross-sectional view of the stent of FIG. 1 in an expanded state within a lumen.

At least a portion of the strut elements 50 of stent 10 may be eventually covered with endothelial cell growth, which may further minimize blood flow interference. This advantage is shown in comparative FIGS. 8A and 8B, both showing a cross-sectional view of a stent in a lumen. FIG. 8A shows a stent 10a with rectangular strut elements 5 (see FIG. 1) in an expanded state. The strut elements 5 of stent 10a have encountered the target obstruction 42, and at least one outer surface 5a is positioned adjacent to the surface 40 of the obstruction 42. The outline of the flow path of stent 10a is shown by the dashed line. As seen from the diagonal lines within the outline of the stent 10a, there is a cross-sectional area A for unrestricted blood flow through the vessel 70.

Figure 8B:
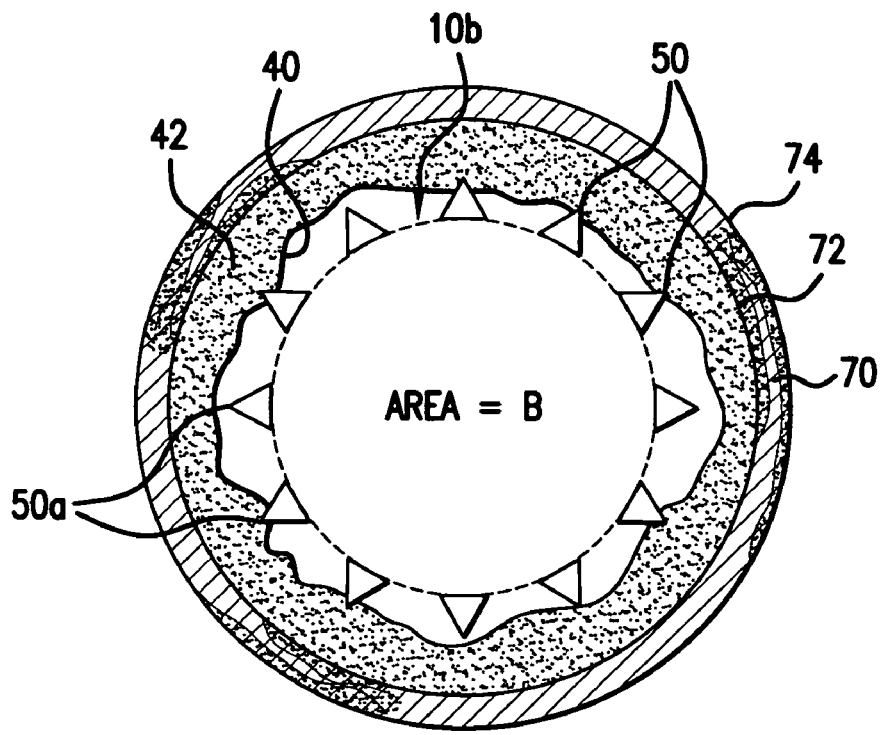
FIG. 8B shows a cross-sectional view of a stent having a shaped strut element in an expanded state within a lumen.

In contrast, FIG. 8B shows a stent 10b with shaped strut elements 50 (see, e.g., FIGS. 3A-3C, 6A-6B) in an expanded state. The strut elements 50 of stent 10b have similarly encountered the target obstruction 42, and at least a portion of the strut elements 50 has penetrated the surface 40 of the obstruction 42 (as shown in FIGS. 5A-5C). The outline of the flow path of stent 10b is again shown by the dashed line, the cross-sectional area B shown by the diagonal lines within the outline. As seen from a comparison of FIGS. 8A and 8B, area B is noticeably larger than area A, which provides for increased unrestricted blood flow through the vessel 70 with which the stent 10b is used with shaped strut elements 50.

Figure 9A:
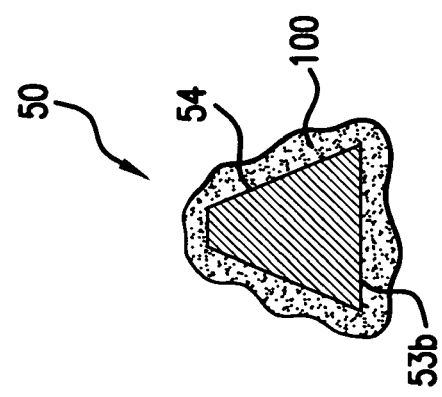
FIGS. 9A-9C show the cross-sectional views of the struts of FIGS. 3A-3C, respectively, wherein the entire cross-sectional surface area of the struts is coated with a coating of a therapeutic agent.
Figure 9B:
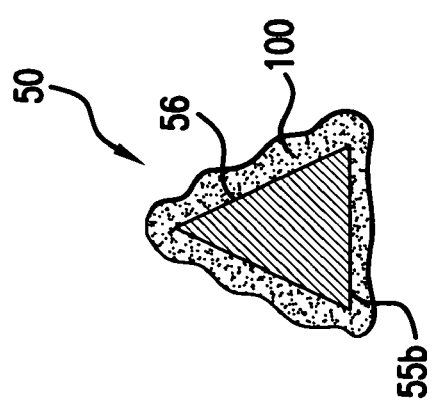
Figure 9C:
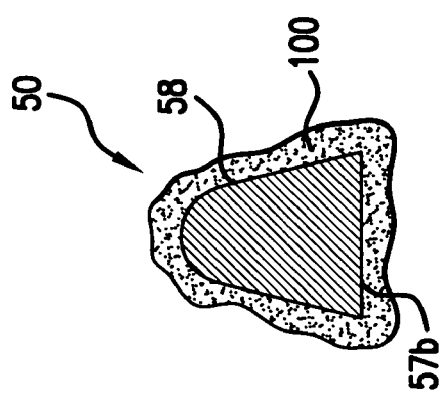

At least a portion of a surface of a strut may be coated with a coating comprising a therapeutic agent. For example, the coating can be disposed on a portion of the outer surface and/or disposed on a portion of one or more side surfaces. FIGS. 9A-9C show the cross-sectional views of the strut elements of FIGS. 3A-3C, respectively, wherein the entire cross-sectional surface area of the strut elements 50 is coated with a coating 100 of a therapeutic agent.

Figure 10A:
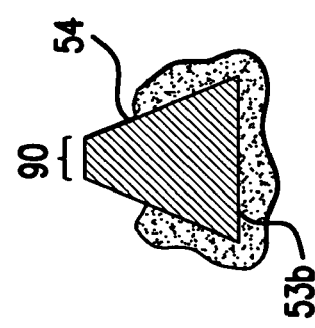
FIGS. 10A-10C show the cross-sectional views of the struts of FIGS. 3A-3C, respectively, wherein part of the cross-sectional surface area of the struts is coated with a coating of a therapeutic agent.
Figure 10B:
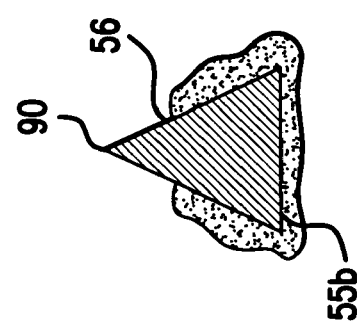
Figure 10C:
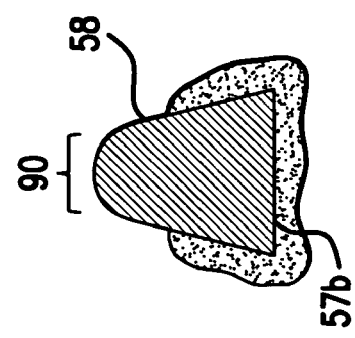

An alternative coating 100 pattern is shown in FIGS. 10A-10C. FIGS. 10A-10C show the cross-sectional views of the strut elements of FIGS. 3A-3C, respectively, wherein part of the cross-sectional surface area of the strut elements 50 coated with a coating 100 of a therapeutic agent. As seen in these embodiments, at least the apex or distal surface 90 of the strut elements 50 may be uncoated, while the remainder of the strut elements 50 surface may be coated with a coating 100. These embodiments may be advantageous when the strut elements 50 are to be inserted into difficult obstructions, such as hardened calcified lesions, during use. When the strut elements 50 are entirely coated with a coating 100, at least a portion of the coating 100 can be scraped off when a portion of the strut 50 is inserted into the obstruction. The embodiments of FIGS. 10A-10C provide for an uncoated apex or distal surface 90 that may more easily be insertable into a difficult obstruction. These embodiments may be especially useful in fields such as interventional cardiology, as it may be the practice in such fields to insert the strut elements 50 into distal lesions first, thereby forcing the strut elements 50 near the proximal portion of the stent 10 to be pushed through proximal lesions first. The embodiments of FIGS. 10A-10C may also be useful in protecting the coating 100 on self-expanding stents enclosed in a sheath or equivalent structure during the delivery process.

The coating 100 pattern of FIGS. 10A-10C may be produced be any suitable method described herein. Laser ablation may be especially useful in ablating unwanted coating from an apex or distal surface 90 of the strut elements 50. Examples and techniques of laser ablation can be found in International Patent No. WO 03039768 for "Method for Coating a Medical Device Using UV Laser to Ablate Excess Coating" to Flanagan, incorporated by reference herein in its entirety. Another method for achieving the coating 100 pattern of FIGS. 10A-10C may be to mask the apex or distal surface 90 of the strut elements 50 during the coating process. Alternatively, the outer surface of the struts may be coated, while the inner surface of the struts are uncoated.

For all the above embodiments, it may be preferable to use more than one therapeutic agent coating 100 on a single strut element 50. For example, it may be preferable to apply a coating of a therapeutic agent on inner surfaces 53b, 55b, 57b that encourage endothelial cell growth, and apply a different therapeutic agent on at least one other surface for the same or different therapeutic purpose. Examples of therapeutic agents that can be used on inner surfaces 53b, 55b, 57b to encourage endothelial cell growth are antibodies CD33 and CD34, which aim to capture progenitor endothelial cells and subsequently cause a thin confluent layer of endothelium to grow quickly on the inner surface 53b, 55b, 57b to assist enveloping the stent 10.

A coating composition may be prepared, for example, by applying a mixture of a polymeric material, a solvent and a therapeutic agent on a surface to form a coating. If such a composition is used the polymeric material incorporates the therapeutic agent. Alternatively, the coating composition may not include a polymeric material. The following is a description of suitable materials and methods useful in producing a coating on the surface of stent struts of the invention.

Polymeric materials useful for forming the coating should be ones that are biocompatible, particularly during insertion or implantation of the device into the body and avoids irritation to body tissue. Examples of such polymers include, but not limited to, polyurethanes, polyisobutylene and its copolymers, silicones, and polyesters. Other suitable polymers include polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers. Since the polymer is being applied to a part of the medical device which undergoes mechanical challenges, e.g. expansion and contraction, the polymers are preferably selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. The polymer is selected to allow the coating to better adhere to the surface of the strut when the stent is subjected to forces or stress. Furthermore, although the coating can be formed by using a single type of polymer, various combinations of polymers can be employed.

Generally, when a biologically active material used is a hydrophilic, e.g., heparin, then a matrix material comprising a more hydrophilic material has a greater affinity for the biologically active material than another matrix material that is less hydrophilic. When a biologically active material used is a hydrophobic, e.g., paclitaxel, actinomycin, sirolimus (RAPAMYCIN), tacrolimus, everolimus, and dexamethasone, then a matrix material that is more hydrophobic has a greater affinity for the biologically active material than another matrix material that is less hydrophobic.

Examples of suitable hydrophobic polymers include, but not limited to, polyolefins, such as polyethylene, polypropylene, poly(1-butene), poly(2-butene), poly(1-pentene), poly(2-pentene), poly(3-methyl-1-pentene), poly(4-methyl-1-pentene), poly(isoprene), poly(4-methyl-1-pentene), ethylene-propylene copolymers, ethylene-propylene-hexadiene copolymers, ethylene-vinyl acetate copolymers, blends of two or more polyolefins and random and block copolymers prepared from two or more different unsaturated monomers; styrene polymers, such as poly(styrene), poly(2-methylstyrene), styrene-acrylonitrile copolymers having less than about 20 mole-percent acrylonitrile, and styrene-2,2,3,3,-tetrafluoropropyl methacrylate copolymers; halogenated hydrocarbon polymers, such as poly(chlorotrifluoroethylene), chlorotrifluoroethylene-tetrafluoroethylene copolymers, poly(hexafluoropropylene), poly(tetrafluoroethylene), tetrafluoroethylene, tetrafluoroethylene-ethylene copolymers, poly(trifluoroethylene), poly(vinyl fluoride), and poly(vinylidene fluoride); vinyl polymers, such as poly(vinyl butyrate), poly(vinyl decanoate), poly(vinyl dodecanoate), poly(vinyl hexadecanoate), poly(vinyl hexanoate), poly(vinyl propionate), poly(vinyl octanoate), poly(heptafluoroisopropoxyethylene), poly(heptafluoroisopropoxypropylene), and poly(methacrylonitrile); acrylic polymers, such as poly (n-butyl acetate), poly(ethyl acrylate), poly(1-chlorodifluoromethyl)tetrafluoroethyl acrylate, poly di(chlorofluoromethyl)fluoromethyl acrylate, poly(1,1-dihydroheptafluorobutyl acrylate), poly(1,1-dihydropentafluoroisopropyl acrylate), poly(1,1-dihydropentadecafluorooctyl acrylate), poly (heptafluoroisopropyl acrylate), poly 5-(heptafluoroisopropoxy)pentyl acrylate, poly 11-(heptafluoroisopropoxy)undecyl acrylate, poly 2-(heptafluoropropoxy)ethyl acrylate, and poly(nonafluoroisobutyl acrylate); methacrylic polymers, such as poly(benzyl methacrylate), poly(n-butyl methacrylate), poly(isobutyl methacrylate), poly(t-butyl methacrylate), poly(t-butylaminoethyl methacrylate), poly(dodecyl methacrylate), poly(ethyl methacrylate), poly(2-ethylhexyl methacrylate), poly(n-hexyl methacrylate), poly(phenyl methacrylate), poly(n-propyl methacrylate), poly(octadecyl methacrylate), poly(1,1-dihydropentadecafluorooctyl methacrylate), poly(heptafluoroisopropyl methacrylate), poly(heptadecafluorooctyl methacrylate), poly(1-hydrotetrafluoroethyl methacrylate), poly(1,1-dihydrotetrafluoropropyl methacrylate), poly(1-hydrohexafluoroisopropyl methacrylate), and poly(t-nonafluorobutyl methacrylate); polyesters, such a poly(ethylene terephthalate) and poly(butylene terephthalate); condensation type polymers such as and polyurethanes and siloxane-urethane copolymers; polyorganosiloxanes, i.e., polymeric materials characterized by repeating siloxane groups, represented by $R_a SiO_{4-a/2}$, where R is a monovalent substituted or unsubstituted hydrocarbon radical and the value of a is 1 or 2; and naturally occurring hydrophobic polymers such as rubber.

Examples of suitable hydrophilic monomer include, but not limited to; (meth)acrylic acid, or alkaline metal or ammonium salts thereof; (meth)acrylamide; (meth)acrylonitrile; those polymers to which unsaturated dibasic, such as maleic acid and fumaric acid or half esters of these unsaturated dibasic acids, or alkaline metal or ammonium salts of these dibasic adds or half esters, is added; those polymers to which unsaturated sulfonic, such as 2-acrylamido-2-methylpropanesulfonic, 2-(meth)acryloylethanesulfonic acid, or alkaline metal or ammonium salts thereof, is added; and 2-hydroxyethyl (meth)acrylate and 2-hydroxypropyl (meth)acrylate.

Polyvinyl alcohol is also an example of hydrophilic polymer. Polyvinyl alcohol may contain a plurality of hydrophilic groups such as hydroxyl, amido, carboxyl, amino, ammonium or sulfonyl ($—SO_3$). Hydrophilic polymers also include, but are not limited to, starch, polysaccharides and related cellulosic polymers; polyalkylene glycols and oxides such as the polyethylene oxides; polymerized ethylenically unsaturated carboxylic acids such as acrylic, mathacrylic and maleic acids and partial esters derived from these acids and polyhydric alcohols such as the alkylene glycols; homopolymers and copolymers derived from acrylamide; and homopolymers and copolymers of vinylpyrrolidone.

The coating layer may also contain one or more biological active materials. A biologically active material can also be included in the structural element. The term "biologically active material" encompasses therapeutic agents, such as biologically active agents, and also genetic materials and biological materials. The genetic materials mean DNA or RNA, including, without limitation, of DNA/RNA encoding a useful protein stated below, intended to be inserted into a human body including viral vectors and non viral vectors as well as anti-sense nucleic acid molecules such as DNA, RNA and RNAi. Viral vectors include adenoviruses, gutted adenoviruses, adeno associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, skeletal myocytes, macrophage), replication competent viruses (e.g., ONYX 015), and hybrid vectors. Non viral vectors include artificial chromosomes and mini chromosomes, plasmid DNA vectors (e.g., pCOR), cationic polymers (e.g., polyethyleneimine, polyethyleneimine (PEI)) graft copolymers (e.g., polyether PEI and polyethylene oxide PEI), neutral polymers PVP, SP1017 (SUPRATEK), lipids or lipoplexes, nanoparticles and microparticles with and without targeting sequences such as the protein transduction domain (PTD). The biological materials include cells, yeasts, bacteria, proteins, peptides, cytokines and hormones. Examples for peptides and proteins include growth factors (FGF, FGF 1, FGF 2, VEGF, Endotherial Mitogenic Growth Factors, and epidermal growth factors, transforming growth factor and platelet derived endothelial growth factor, platelet derived growth factor, tumor necrosis factor, hepatocyte growth factor and insulin like growth factor), transcription factors, proteinkinases, CD inhibitors, thymidine kinase, and bone morphogenic proteins (BMP's), such as BMP 2, BMP 3, BMP 4, BMP 5, BMP 6 (Vgr 1), BMP 7 (OP 1), BMP 8, BMP 9, BMP 10, BMP 11, BMP 12, BMP 13, BMP 14, BMP 15, and BMP 16. Currently preferred BMP's are BMP 2, BMP 3, BMP 4, BMP 5, BMP 6, BMP 7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include whole bone marrow, bone marrow derived mono nuclear cells, progenitor cells (e.g., endothelial progenitor cells) stem cells (e.g., mesenchymal, hematopoietic, neuronal), pluripotent stem cells, fibroblasts, macrophage, and satellite cells.

Biologically active material also includes non genetic therapeutic agents, such as:
  anti thrombogenic agents such as heparin, heparin derivatives, urokinase, and PPack (dextrophenylalanine proline arginine chloromethylketone);
  anti proliferative agents such as enoxaprin, angiopeptin, or monoclonal antibodies capable of blocking smooth muscle cell proliferation, hirudin, acetylsalicylic acid, tanolimus, everolimus, amlodipine and doxazosin;
  anti inflammatory agents such as glucocorticoids, betamethasone, dexamethasone, prednisolone, corticosterone, budesonide, estrogen, sulfasalazine, rosiglitazone, mycophenolic acid, and mesalamine;
  antineoplastic/antiproliferative/antimiotic agents such as paclitaxel or analogs or derivatives thereof, 5 fluorouracil, cisplatin, vinblastine, vincristine, epothilones, methotrexate, azathioprine, adriamycin and mutamycin; endostatin, angiostatin and thymidine kinase inhibitors, cladribine;
  anesthetic agents such as lidocaine, bupivacaine, and ropivacaine;
  anticoagulants such as D Phe Pro Arg chloromethyl keton, an RGD peptide containing compound, heparin, antithrombin compounds, platelet receptor antagonists, anti thrombin antibodies, anti platelet receptor antibodies, aspirin (aspirin is also classified as an analgesic, antipyretic and anti inflammatory drug), dipyridamole, protamine, hirudin, prostaglandin inhibitors, antiplatelet agents such as trapidil or liprostin, platelet inhibitors and tick antiplatelet peptides;
  vascular cell growth promotors such as growth factors, Vascular Endothelial Growth Factors (FEGF, all types including VEGF 2), growth factor receptors, transcriptional activators, and translational promotors;
  DNA demethylating drug such as 5-azacytidine, which is also categorized as a RNA or DNA metabolite that inhibit cell growth and induce apoptosis in certain cancer cells;
  vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol lowering agents; vasodilating agents; and agents which interfere with endogenous vasoactive mechanisms;

antioxidants, such as probucol;

antibiotic agents, such as penicillin, cefoxitin, oxacillin, tobranycin, rapamycin (sirolimus);

angiogenic substances, such as acidic and basic fibrobrast growth factors, estrogen including estradiol (E2), estriol (E3) and 17 Beta Estradiol;

smooth muscle cell proliferation inhibitors, such as rapamycin; and drugs for heart failure, such as digoxin, beta blockers, angiotensin converting enzyme (ACE) inhibitors including captopril and enalopril, statins and related compounds;

macrolides such as sirolimus, or everolimus or tacrolimus; and other suitable therapeutic agents include halofuginone, inhibitors of HSP 90 protein such as geldanamycin, microtubule stabilizing agents such as epothilone D, and phosphodiesterase inhibitors such as cilostrazole.

Preferred biologically active materials include anti proliferative drugs such as steroids, vitamins, and restenosis inhibiting agents. Preferred restenosis inhibiting agents include microtubule stabilizing agents such as paclitaxel, paclitaxel analogues, derivatives, and mixtures thereof. For example, derivatives suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

Other preferred biologically active materials include nitroglycerin, nitrous oxides, nitric oxides, antibiotics, aspirins, digitalis, estrogen derivatives such as estradiol and glycosides.

The solvent that is used to form the coating composition include ones which can dissolve the polymer into solution and do not alter or adversely impact the therapeutic properties of the therapeutic agent employed. Examples of useful solvents include tetrahydrofuran (THF), methyl ethyl ketone chloroform, toluene, acetone, issoctane, 1,1,1-trichloroethane, isoppropanol, IPA and dichloromethane or mixtures thereof.

In one method of forming the aforementioned coating layers, a coating material composition is applied to the surface. Coating compositions can be applied by any method to a surface of a medical device to form a coating layer. Examples of suitable methods include, but are not limited to, spraying such as by conventional nozzle or ultrasonic nozzle, dipping, rolling, electrostatic deposition, and a batch process such as air suspension, pan coating or ultrasonic mist spraying. Also, more than one coating method can be used to make a medical device. Coating compositions suitable for applying a coating to the devices of the present invention can include a polymeric material dispersed or dissolved in a solvent suitable for the medical device, wherein upon applying the coating composition to the medical device, the solvent is removed. Such systems are commonly known to the skilled artisan.

A coating of a medical device of the present invention may include multiple coating layers. For example, the first layer and the second layer may contain different biologically active materials. Alternatively, the first layer and the second layer may contain an identical biologically active material having different concentrations. In one embodiment, either of the first layer or the second layer may be free of biologically active material. For example, when the biologically active solution is applied onto a surface and dried (the first layer), a coating composition free of a biologically active material (the second layer) can be applied over the dried biologically active material.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein by reference, in their entirety, for all purposes related to this disclosure.

What is claimed:

1. A stent for implantation in a body lumen comprising:
   (a) at least one strut having an inner surface, an outer surface, a first side surface disposed between the inner surface and the outer surface, and a second side surface disposed between the inner surface and the outer surface;
   wherein the first side surface and the second side surface converge toward one another in the direction of the outer surface;
   a coating comprising a first therapeutic agent to encourage endothelial cell growth disposed only on the inner surface of the strut; and
   a second therapeutic agent that is different from the first therapeutic agent, the second therapeutic agent disposed on at least a portion of the first side surface or second side surface.

2. The stent of claim 1 wherein the second therapeutic agent is further disposed on at least a portion of the outer surface.

3. The stent of claim 1 wherein the second therapeutic agent is disposed on at least a portion of the first side surface and at least a portion of the second side surface.

4. The stent of claim 1 wherein the strut comprises a cross-section having a substantially trapezoidal shape.

5. The stent of claim 4 wherein first side surface and the second side surface form the sides of the substantially trapezoidal shape.

6. The stent of claim 1 wherein the outer surface is substantially curved.

7. The stent of claim 1 wherein the strut comprises a cross-section having a substantially triangular shape.

8. The stent of claim 7 wherein first side surface and the second side surface form the sides of the substantially triangular shape.

9. The stent of claim 1 wherein at least one of the first or second therapeutic agents comprises paclitaxel, an analog of paclitaxel or a derivative of paclitaxel.

10. The stent of claim 1 wherein at least one of the first or second therapeutic agents comprise a macrolide selected from the group consisting of sirolimus, tacrolimus, or everolimus.

11. The stent of claim 1 wherein the coating further comprises a polymeric material.

12. The stent of claim 11 wherein the polymeric material incorporates at least the first therapeutic agent.

13. The stent of claim 1 wherein the stent is an intravascular stent.

14. The stent of claim 1 wherein the strut further comprises a third side surface disposed between the inner surface and the outer surface and in contact with the inner surface, and a fourth side surface disposed between the inner surface and the outer surface and in contact with the inner surface.

15. The stent of claim 1 wherein the first therapeutic agent comprises antibodies CD33 or CD34.

16. A stent for implantation in a body lumen comprising:
(a) at least one strut having an inner surface, an outer surface, a first side surface disposed between the inner surface and the outer surface, and a second side surface disposed between the inner surface and the outer surface;
wherein the first side surface and the second side surface converge toward one another in the direction of the outer surface;
(b) a first coating comprising a first therapeutic agent and a first polymeric material disposed on at least a portion of the outer surface, a portion of the first side surface, and a portion of the second side surface; and
(c) a second coating comprising a second therapeutic agent and a second polymeric material disposed only on the inner surface;
wherein the first therapeutic agent has a different therapeutic purpose than that on the second therapeutic agent; and
wherein the purpose of the second therapeutic agent is to encourage endothelial cell growth.

17. The stent of claim 16 wherein at least one of the first or second therapeutic agents comprise paclitaxel, an analog of paclitaxel or a derivative of paclitaxel.

18. The stent of claim 16 wherein at least one of the first or second therapeutic agents comprise a macrolide selected from the group consisting of sirolimus, tacrolimus, or everolimus.

* * * * *

UNITED STATES PATENT AND TRADEMARK OFFICE
CERTIFICATE OF CORRECTION

PATENT NO. : 7,628,807 B2 Page 1 of 1
APPLICATION NO. : 10/982356
DATED : December 8, 2009
INVENTOR(S) : Aiden Flanagan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 400 days.

Signed and Sealed this

Second Day of November, 2010

David J. Kappos
*Director of the United States Patent and Trademark Office*